(12) United States Patent
Kim

(10) Patent No.: US 11,079,572 B2
(45) Date of Patent: Aug. 3, 2021

(54) OPTICAL IMAGING SYSTEM HAVING PRISM, FIXED LENS GROUPS, MOVABLE LENS GROUPS AND CORRECTION LENS GROUP

(71) Applicant: Samsung Electro-Mechanics Co., Ltd., Suwon-si (KR)

(72) Inventor: Hag Chul Kim, Suwon-si (KR)

(73) Assignee: Samsung Electro-Mechanics Co., Ltd., Suwon-si (KR)

(*) Notice: Subject to any disclaimer, the term of this patent is extended or adjusted under 35 U.S.C. 154(b) by 5 days.

(21) Appl. No.: 16/460,232

(22) Filed: Jul. 2, 2019

(65) Prior Publication Data
US 2019/0328441 A1 Oct. 31, 2019

Related U.S. Application Data

(62) Division of application No. 15/098,989, filed on Apr. 7, 2016, now Pat. No. 10,386,615.

(30) Foreign Application Priority Data

Oct. 14, 2015 (KR) .......... 10-2015-0143647

(51) Int. Cl.
*G02B 15/167* (2006.01)
*G02B 15/177* (2006.01)
(Continued)

(52) U.S. Cl.
CPC ........ *G02B 13/0065* (2013.01); *A61B 18/042* (2013.01); *A61B 18/1402* (2013.01);
(Continued)

(58) Field of Classification Search
CPC ........ G02B 15/14; G02B 15/15; G02B 15/16; G02B 15/163; G02B 15/167; G02B 15/17;
(Continued)

(56) References Cited

U.S. PATENT DOCUMENTS 6,392,816 B1 5/2002 Hamano
7,068,429 B1 6/2006 Ori
(Continued)

FOREIGN PATENT DOCUMENTS

CN 101071196 A 11/2007
CN 100380162 C 4/2008
(Continued)

OTHER PUBLICATIONS

Chinese Office Action dated Oct. 18, 2019 in counterpart Chinese Patent Application No. 201610260730.4 (12 pages in English, 6 pages in Chinese).

(Continued)

*Primary Examiner* — Ryan S Dunning
(74) *Attorney, Agent, or Firm* — NSIP Law

(57) ABSTRACT

There is provided an optical imaging system including a prism, a first fixed lens group, a first movable lens group, a second movable lens group, and a second fixed lens group. The prism is configured to refract light reflected from an object side toward an imaging plane and a reflecting member. The prism is disposed on the first fixed lens group and the first movable lens group is configured to change a position of the imaging plane so that an overall focal length is changed. The second movable lens group is configured to adjust a position of the imaging plane so that a focal length for an object is adjusted. The imaging plane is disposed on the second fixed lens group.

18 Claims, 14 Drawing Sheets

(51) Int. Cl.
  *G02B 15/20* (2006.01)
  *G02B 13/00* (2006.01)
  *A61B 18/04* (2006.01)
  *A61B 18/14* (2006.01)
  *G02B 15/14* (2006.01)
  *G02B 27/64* (2006.01)
  *A61B 18/00* (2006.01)

(52) U.S. Cl.
  CPC ......... *G02B 13/002* (2013.01); *G02B 13/006* (2013.01); *G02B 15/144* (2019.08); *G02B 27/646* (2013.01); *A61B 2018/00744* (2013.01); *G02B 15/167* (2013.01)

(58) Field of Classification Search
  CPC ........ G02B 15/173; G03B 3/00; G03B 13/32; G03B 2205/0046
  USPC ................................ 359/676, 678, 683–688
  See application file for complete search history.

(56) References Cited

U.S. PATENT DOCUMENTS

| | | |
|---|---|---|
| 2004/0095503 A1 | 5/2004 | Iwasawa et al. |
| 2006/0051082 A1 | 3/2006 | Tamura |
| 2006/0067662 A1 | 3/2006 | Satori |
| 2006/0280498 A1 | 12/2006 | Souma et al. |
| 2007/0008418 A1 | 1/2007 | Kuroda et al. |
| 2007/0053079 A1 | 3/2007 | Nanjo et al. |
| 2007/0097508 A1 | 5/2007 | Ohtake et al. |
| 2007/0126911 A1 | 6/2007 | Nanjo |
| 2007/0285520 A1 | 12/2007 | Kuroda |
| 2008/0247053 A1 | 10/2008 | Iwasawa |
| 2009/0180183 A1 | 7/2009 | Heu |
| 2010/0103539 A1 | 4/2010 | Kitahara |
| 2011/0194015 A1 | 8/2011 | Kanetaka |
| 2012/0212836 A1 | 8/2012 | Hsieh et al. |
| 2012/0307376 A1 | 12/2012 | Kakimoto |
| 2013/0050464 A1 | 2/2013 | Kang |
| 2013/0050535 A1 | 2/2013 | Kuroda et al. |
| 2013/0278785 A1 | 10/2013 | Nomura et al. |
| 2014/0063604 A1 | 3/2014 | Wada |
| 2014/0152887 A1 | 6/2014 | Hagiwara |
| 2014/0267877 A1* | 9/2014 | Nakagawa ............. G02B 15/14 348/335 |
| 2015/0022908 A1 | 1/2015 | Tomioka |
| 2015/0198792 A1 | 7/2015 | Kawana |
| 2015/0212337 A1 | 7/2015 | Nomura et al. |
| 2015/0215542 A1 | 7/2015 | Nomura et al. |

FOREIGN PATENT DOCUMENTS

| | | |
|---|---|---|
| CN | 100426043 C | 10/2008 |
| CN | 201503514 U | 6/2010 |
| CN | 102147520 A | 8/2011 |
| CN | 102967927 A | 3/2013 |
| CN | 102967929 A | 3/2013 |
| CN | 103376613 A | 10/2013 |
| CN | 103852875 A | 6/2014 |
| CN | 104793323 A | 7/2015 |
| CN | 104865773 A | 8/2015 |
| CN | 104865774 A | 8/2015 |
| JP | 2001-124992 A | 5/2001 |
| JP | 2008-197411 A | 8/2008 |
| JP | 2014-48622 A | 3/2014 |
| JP | 5671190 B2 | 12/2014 |
| KR | 10-2007-0052213 A | 5/2007 |
| KR | 10-2009-0077517 A | 7/2009 |
| KR | 10-2010-0018339 A | 2/2010 |
| KR | 10-2011-0071807 A | 6/2011 |
| KR | 10-2014-0003368 A | 1/2014 |

OTHER PUBLICATIONS

Korean Office Action dated Nov. 25, 2016 in corresponding Korean patent application No. 10-2015-0143647 (16 pages with English translation).

Chinese Office Action dated Jun. 29, 2018 in counterpart Chinese Patent Application No. 201610260730.4 (34 pages, in Chinese with English translation).

* cited by examiner

| FIRST EMBODIMENT | | | | |
|---|---|---|---|---|
| fw = | 4.80 | | ft = | 13.56 |
| F #w = | 2.75 | | F #t = | 3.69 |
| SURFACE NO. | | RADIUS OF CURVATURE | THICKNESS /DISTANCE | REFRACTIVE INDEX(ni) | ABBE NUMBER(vi) |
| S1 | FIRST LENS | 38.1431 | 0.3000 | 2.001 | 25.458 |
| S2 | | 10.3400 | 1.3400 | | |
| S3 | PRISM | infinity | 3.2000 | 2.001 | 29.134 |
| S4 | | infinity | 3.2000 | 2.001 | 29.134 |
| S5 | | infinity | 0.2010 | | |
| S6 | SECOND LENS | 14.9950 | 1.6300 | | 49.241 |
| S7 | | -16.8851 | D1 | | |
| S10 | FOURTH LENS | -9.5000 | 0.3400 | 1.768 | 49.222 |
| S11 | FIFTH LENS | 12.1001 | 0.7200 | 2.003 | 19.317 |
| S12 | | 193.5250 | D2 | | |
| S13 | SIXTH LENS | 8.1787 | 1.0800 | 1.497 | 81.560 |
| S14 | | 13.3899 | 0.2000 | | |
| S15 | SEVENTH LENS | 254.5931 | 0.5500 | 1.847 | 23.785 |
| S16 | | 195.8222 | 0.3500 | | |
| S17 | STOP | infinity | D3 | | |
| S18 | EIGHTH LENS | 5.2084 | 2.0570 | 1.497 | 81.560 |
| S19 | | -9.4057 | 0.1000 | | |
| S20 | NINTH LENS | 5.7221 | 1.8090 | 1.697 | 55.460 |
| S21 | TENTH LENS | -11.0093 | 0.5000 | 1.911 | 35.250 |
| S22 | | 3.4851 | D4 | | |
| S23 | ELEVENTH LENS | 14.6209 | 1.0800 | 1.540 | 56.000 |
| S24 | | -71.2363 | 0.3000 | | |
| S25 | REFLECTING MEMBER | infinity | 4.2000 | | |
| S26 | FILTER | infinity | 0.5000 | | |
| S27 | | infinity | 0.5000 | 1.519 | 64.0 |
| S28 | IMAGING PLANE | infinity | D5 | | |

FIG. 5

|    | WIDE ANGLE END | INTERMEDIATE END | TELEPHOTO END |
|----|----------------|------------------|---------------|
| D1 | 0.318          | 3.381            | 6.673         |
| D2 | 6.72           | 3.657            | 0.365         |
| D3 | 5.731          | 4.166            | 2.666         |
| D4 | 0.8            | 2.365            | 3.864         |
| D5 | 0.409          | 0.397            | 0.408         |

FIG. 6

| SURFACE NO. | K | A | B | C | D | E | F | G | H |
|---|---|---|---|---|---|---|---|---|---|
| S6 | 0.000E+00 | -1.516E-05 | -2.782E-06 | 2.207E-07 | -5.359E-09 | 0.00000 | 0.00000 | 0.00000 | 0.00000 |
| S7 | 0.000E+00 | 5.631E-05 | -2.085E-06 | 1.900E-07 | -4.878E-09 | 0.00000 | 0.00000 | 0.00000 | 0.00000 |
| S13 | -3.926E+00 | -3.182E-04 | -5.815E-05 | 1.150E-06 | -1.757E-07 | 0.00000 | 0.00000 | 0.00000 | 0.00000 |
| S14 | -5.000E+00 | -5.817E-04 | -5.617E-05 | 4.972E-06 | -5.081E-07 | 0.00000 | 0.00000 | 0.00000 | 0.00000 |
| S18 | 0.000E+00 | -7.190E-04 | 1.723E-06 | -1.111E-06 | 8.772E-08 | 0.00000 | 0.00000 | 0.00000 | 0.00000 |
| S19 | 0.000E+00 | 7.784E-04 | 2.104E-06 | -2.177E-07 | 9.528E-08 | 0.00000 | 0.00000 | 0.00000 | 0.00000 |
| S23 | -2.339E+01 | 9.548E-04 | -3.744E-04 | 4.287E-05 | -3.582E-06 | 0.00000 | 0.00000 | 0.00000 | 0.00000 |
| S24 | 2.500E+01 | -1.307E-04 | -3.229E-04 | 3.421E-05 | -2.669E-06 | 0.00000 | 0.00000 | 0.00000 | 0.00000 |

FIG. 7

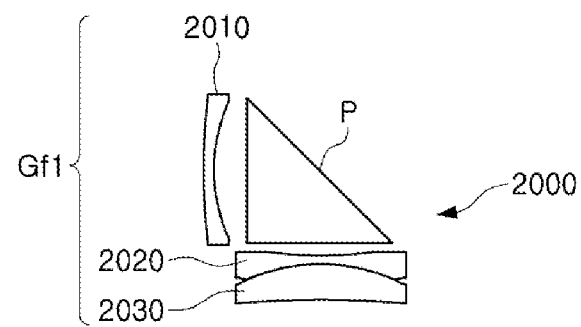
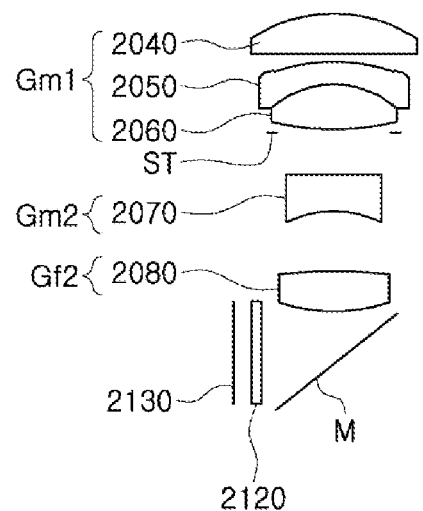
FIG. 8

| SECOND EMBODIMENT | | | | | |
|---|---|---|---|---|---|
| fw = | 4.90 | fm = | 7.80 | ft = | 13.70 |
| F #w = | 2.80 | F #m = | 3.70 | F #t = | 5.70 |

| SURFACE NO. | | RADIUS OF CURVATURE | THICKNESS /DISTANCE | REFRACTIVE INDEX(ni) | ABBE NUMBER(vi) |
|---|---|---|---|---|---|
| S1 | FIRST LENS | 21.4160 | 0.3000 | 1.729 | 54.700 |
| S2 | | 5.2280 | 1.2200 | | |
| S3 | | infinity | 2.3900 | 1.911 | 35.250 |
| S4 | PRISM | infinity | 2.3900 | 1.911 | 35.250 |
| S5 | | infinity | 0.3300 | | |
| S6 | SECOND LENS | -28.6000 | 0.3000 | | 63.520 |
| S7 | THIRD LENS | 5.5410 | 1.1600 | 1.911 | 35.250 |
| S10 | | -73.5220 | 0.3800 | 1.620 | |
| S11 | FIFTH LENS | 5.8970 | 0.5100 | 1.913 | 32.360 |
| S12 | SIXTH LENS | 3.0740 | 1.4800 | 1.497 | 81.610 |
| S13 | | -8.5960 | 0.1000 | | |
| S14 | STOP | Infinity | D2 | | |
| S15 | SEVENTH LENS | -18.8650 | 1.1000 | 1.531 | 55.750 |
| S16 | | 3.4790 | D3 | | |
| S17 | EIGHTH LENS | 26.1550 | 1.3300 | 1.531 | 55.750 |
| S18 | | -7.0000 | 0.0000 | | |
| S19 | REFLECTING MEMBER | infinity | 4.3000 | | |
| S20 | FILTER | infinity | 0.1100 | 1.517 | 64.200 |
| S21 | | infinity | 0.5000 | | |
| S22 | IMAGING PLANE | infinity | | | |

FIG. 12

|    | WIDE ANGLE END | INTERMEDIATE END | TELEPHOTO END |
|----|----------------|------------------|---------------|
| D1 | 7.16           | 3.79             | 0.4           |
| D2 | 1.63           | 2.38             | 4.53          |
| D3 | 1.45           | 4.06             | 5.32          |

FIG. 13

| SURFACE NO. | K | A | B | C | D | E | F | G | H |
|---|---|---|---|---|---|---|---|---|---|
| S9 | 2.133E-01 | -4.211E-04 | -2.900E-05 | 2.930E-06 | -3.974E-07 | 0.000000 | 0.000000 | 0.000000 | 0.000000 |
| S10 | -9.900E+01 | 1.657E-03 | -7.789E-06 | 2.286E-06 | -2.888E-07 | 0.000000 | 0.000000 | 0.000000 | 0.000000 |
| S15 | -4.542E+01 | -1.195E-03 | -4.047E-04 | 1.387E-04 | -8.215E-06 | 0.000000 | 0.000000 | 0.000000 | 0.000000 |
| S16 | -5.356E+00 | 1.609E-02 | -3.326E-03 | 7.219E-04 | -7.271E-05 | 0.000000 | 0.000000 | 0.000000 | 0.000000 |
| S17 | 4.357E+01 | 2.113E-03 | -8.998E-05 | -3.389E-06 | 1.036E-06 | 0.000000 | 0.000000 | 0.000000 | 0.000000 |
| S18 | -1.067E+01 | -1.441E-03 | 3.224E-04 | -3.815E-05 | 2.508E-06 | 0.000000 | 0.000000 | 0.000000 | 0.000000 |

FIG. 14

OPTICAL IMAGING SYSTEM HAVING PRISM, FIXED LENS GROUPS, MOVABLE LENS GROUPS AND CORRECTION LENS GROUP

CROSS-REFERENCE TO RELATED APPLICATIONS

This application is a divisional of U.S. patent application Ser. No. 15/092,989 filed on Apr. 7, 2016, now U.S. Pat. No. 10,386,615 issued on Aug. 20, 2019, which claims the benefit under 35 USC 119(a) of Korean Patent Application No. 10-2015-0143647 filed on Oct. 14, 2015, in the Korean Intellectual Property Office, the entire disclosures of which are incorporated herein by reference for all purposes.

BACKGROUND

1. Field

The following description relates to an optical imaging system of which a focal length may be adjusted.

2. Description of Related Art

In a needle case type optical imaging system, in which a plurality of lenses are disposed linearly or in a row, as a number of lenses is increased, an overall length of the optical imaging system is increased. For example, it is more difficult to miniaturize an optical imaging system including five lenses than to miniaturize an optical imaging system including three lenses. For this reason, there is a limitation in mounting needle case type optical imaging systems in small portable terminals.

Conversely, in a curved optical imaging system, only some lenses are disposed in a row. Therefore, curved optical imaging systems may be mounted in tight spaces. However, because the curved optical imaging system uses a plurality of refracting prisms, manufacturing costs of the optical imaging system are high, and optical performance of the optical imaging system may be deteriorated.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided an optical imaging system, including: a prism configured to refract light reflected from an object side toward an imaging plane and a reflecting member; a first fixed lens group in which the prism is disposed; a first movable lens group configured to change a position of the imaging plane so that an overall focal length is changed; a second movable lens group configured to adjust a position of the imaging plane so that a focal length for an object is adjusted; and a second fixed lens group in which the imaging plane is disposed.

The first fixed lens group may include two or more lenses having different refractive powers.

The first fixed lens group may include: a first lens adjacently disposed to an object-side surface of the prism and having a negative refractive power; and a second lens adjacently disposed to an image-side surface of the prism and having a positive refractive power.

The first movable lens group may include lenses having different refractive powers.

The second movable lens group may include a lens having a negative refractive power.

The second movable lens group may include a lens including a concave object-side surface and a concave image-side surface.

The second fixed lens group may include a lens having a positive refractive power.

The second fixed lens group may include a lens including a convex object-side surface and a convex image-side surface.

The optical imaging system may also include a stop disposed between the first movable lens group and the second movable lens group.

$2.0 < ft/fw$, in which ft may be an overall focal length at a telephoto end, and fw may be an overall focal length at a wide angle end.

$np < 2.1$, in which np may be a refractive index of the prism.

$4.5 < BFL$, in which BFL may be a distance from an image-side surface of a lens closest to the imaging plane in the second fixed lens group to the imaging plane.

$Yh/(IMG\ HT) < 0.55$, in which Yh may be ½ of a length of a short side of the imaging plane, and IMG HT may be ½ of a diagonal length of the imaging plane.

In accordance with another embodiment, there is provided an optical imaging system, including: a first fixed lens group including lenses; a prism disposed between the lenses of the first fixed lens group; a first movable lens group configured to be movable; a second movable lens group configured to be movable; a stop disposed between the first movable lens group and the second movable lens group; a second fixed lens group including a lens having a positive refractive power; and a reflecting member reflecting light irradiated from the second fixed lens group to an imaging plane.

The prism and the reflecting member may be disposed in a symmetrical form.

The first movable lens group may include a cemented lens.

In accordance with a further embodiment, there is provided an optical imaging system, including: a first fixed lens group including lenses having different refractive powers; a prism disposed between the lenses of the first fixed lens group; a first movable lens group configured to be movable to change an overall focal length; a correction lens group configured to move in an optical axis direction or a direction intersecting with the optical axis; a second movable lens group configured to be movable to finely adjust the overall focal length; and a second fixed lens group, wherein a distance between the first movable lens group and the correction lens group is longest at a wide angle end and is shortest at a telephoto end, and wherein a distance between the correction lens group and the second movable lens group is longest at the wide angle end and shortest at the telephoto end.

A distance between the first fixed lens group and the first movable lens group may be shortest at the wide angle end and may be longest at the telephoto end.

A distance between the second movable lens group and the second fixed lens group are shortest at the wide angle end and longest at the telephoto end.

A distance between the second fixed lens group and the image sensor may be constant or substantially constant.

$4.5 < BFL$, in which BFL may be a distance from an image-side surface of a lens closest to an imaging plane in the second fixed lens group to the imaging plane.

Other features and aspects will be apparent from the following detailed description, the drawings, and the claims.

BRIEF DESCRIPTION OF DRAWINGS

These and/or other aspects will become apparent and more readily appreciated from the following description of the embodiments, taken in conjunction with the accompanying drawings in which:

FIG. 5 is a table illustrating characteristics of lenses of the optical imaging system, according to the first embodiment;

FIG. 6 is a table illustrating distances D1 to D5 between lens groups changed depending on a wide angle end, an intermediate end, and a telephoto end;

FIG. 7 is a table illustrating aspherical characteristics of the optical imaging system, according to the first embodiment;

FIG. 8 is a view of an optical imaging system, according to a second embodiment;

FIG. 12 is a table illustrating characteristics of lenses of the optical imaging system, according to the second embodiment;

FIG. 13 is a table illustrating distances D1 to D5 between lens groups changed depending on the wide angle end, the intermediate end, and the telephoto end; and FIG. 14 is a table illustrating aspherical characteristics of the optical imaging system, according to the second embodiment.

Figure 1:
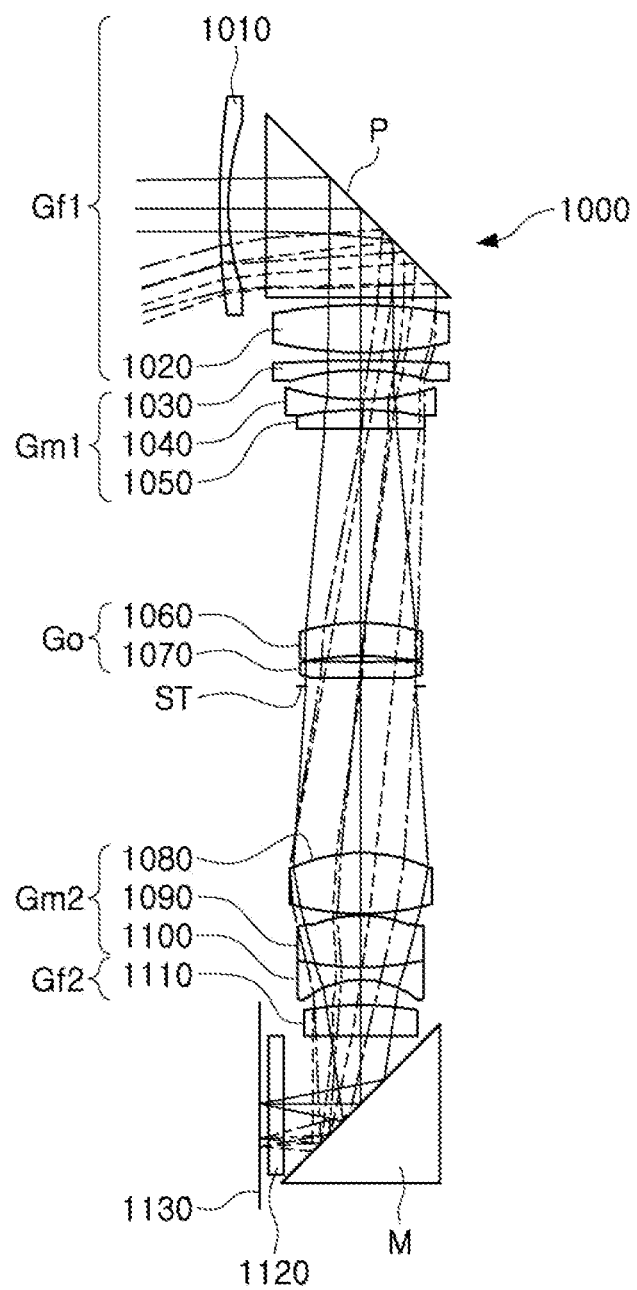
FIG. 1 is a view of an optical imaging system, according to a first embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Throughout the specification, it will be understood that when an element, such as a layer, region or wafer (substrate), is referred to as being "on," "connected to," or "coupled to" another element, it can be directly "on," "connected to," or "coupled to" the other element or other elements intervening therebetween may be present. In contrast, when an element is referred to as being "directly on," "directly connected to," or "directly coupled to" another element, there may be no elements or layers intervening therebetween. Like numerals refer to like elements throughout. As used herein, the term "and/or" includes any and all combinations of one or more of the associated listed items.

It will be apparent that though the terms first, second, third, etc. may be used herein to describe various members, components, regions, layers and/or sections, these members, components, regions, layers and/or sections should not be limited by these terms. These terms are only used to distinguish one member, component, region, layer or section from another region, layer or section. Thus, a first member, component, region, layer or section discussed below could be termed a second member, component, region, layer or section without departing from the teachings of the embodiments.

Spatially relative terms, such as "above," "upper," "below," and "lower" and the like, may be used herein for ease of description to describe one element's relationship to another element(s) as shown in the figures. It will be understood that the spatially relative terms are intended to encompass different orientations of the device in use or operation in addition to the orientation depicted in the figures. For example, if the device in the figures is turned over, elements described as "above," or "upper" other elements would then be oriented "below," or "lower" the other elements or features. Thus, the term "above" can encompass both the above and below orientations depending on a particular direction of the figures. The device may be otherwise oriented (rotated 90 degrees or at other orientations) and the spatially relative descriptors used herein may be interpreted accordingly.

The terminology used herein is for describing particular embodiments only and is not intended to be limiting of the embodiments. As used herein, the singular forms "a," "an," and "the" are intended to include the plural forms as well, unless the context clearly indicates otherwise. It will be further understood that the terms "comprises," and/or "comprising" when used in this specification, specify the presence of stated features, integers, steps, operations, members, elements, and/or groups thereof, but do not preclude the presence or addition of one or more other features, integers, steps, operations, members, elements, and/or groups thereof.

Hereinafter, embodiments will be described with reference to schematic views illustrating various embodiments. In the drawings, for example, due to manufacturing techniques and/or tolerances, modifications of the shape shown may be estimated. Thus, embodiments should not be construed as being limited to the particular shapes of regions shown herein, for example, to include a change in shape results in manufacturing. The following embodiments may also be constituted by one or a combination thereof.

The various embodiments described below may have a variety of configurations and propose only a required configuration herein, but are not limited thereto.

In addition, a surface of each lens closest to an object is referred to as a first surface or an object-side surface, and a surface of each lens closest to an imaging surface is referred to as a second surface or an image-side surface. A first lens is a lens closest to an object (or a subject), while an eleventh lens or an eighth lens is a lens closest to an imaging plane (or an image sensor). A person skilled in the relevant art will appreciate that other units of measurement may be used. Further, in the present specification, all radii of curvature, thicknesses, OALs (optical axis distances from the first surface of the first lens to the image sensor (OALs), a distance on the optical axis between the stop and the image sensor (SLs), image heights or ½ of a diagonal length of the imaging plane (IMGHs) (image heights), and black focus lengths (BFLs) (back focus lengths) of the lenses, an overall focal length of an optical system, and a focal length of each lens are indicated in millimeters (mm). Further, thicknesses of lenses, gaps between the lenses, OALs, and SLs are distances measured based on an optical axis of the lenses. Further, thicknesses of the lenses, gaps between the lenses, and TTL, a through-the-lens, are distances in optical axes through the lenses. The TTL is a camera feature in which light levels are measured through the lens that captures the pictures, as opposed to a separate metering window.

Further, surface of a lens being convex means that an optical axis portion of a corresponding surface is convex, and a surface of a lens being concave means that an optical axis portion of a corresponding surface is concave. Therefore, even in the case that one surface of a lens is described as being convex, an edge portion of the lens may be concave. Likewise, even in the case that one surface of a lens is described as being concave, an edge portion of the lens may be convex. In other words, a paraxial region of a lens may be convex, while the remaining portion of the lens outside the paraxial region is either convex, concave, or flat. Further, a paraxial region of a lens may be concave, while the remaining portion of the lens outside the paraxial region is either convex, concave, or flat.

In the optical system, according to embodiments, the lenses are formed of materials including glass, plastic or other similar types of polycarbonate materials. In another embodiment, at least one of the lenses is formed of a material different from the materials forming the other lenses.

An optical imaging system includes an optical system including lenses. For example, the optical system of the optical imaging system may include lenses having refractive power. However, the optical imaging system is not limited to including only the lenses having refractive power. For example, the optical imaging system may include a stop to control an amount of light. In addition, the optical imaging system may further include an infrared cut-off filter filtering infrared light. Further, the optical imaging system may further include an image sensor, such as an imaging device, configured to convert an image of a subject incident thereto through the optical system into electrical signals. Further, the optical imaging system may further include a gap maintaining member adjusting a gap between lenses.

The lenses are formed of a material having a refractive index different from that of air. For example, the lenses are formed of plastic or glass. At least one of the lenses has an aspherical shape. An aspherical surface of each of the lenses is represented by the following Equation 1:

$$Z = \frac{cr^2}{1 + \sqrt{1-(1+k)c^2r^2}} + Ar^4 + Br^6 + Cr^8 + Dr^{10} + Er^{12} + Fr^{14} + Gr^{16} + Hr^{18} + Jr^{20}$$ [Equation 1]

In this equation, c is an inverse of a radius of curvature of the lens, k is a conic constant, r is a distance from a certain point on an aspherical surface of the lens to an optical axis, A to J are aspherical constants, and Z (or SAG) is a distance between the certain point on the aspherical surface of the lens at the distance Y and a tangential plane meeting the apex of the aspherical surface of the lens.

The optical imaging system, in accordance with an embodiment, includes a plurality of lens groups. For example, the optical imaging system includes a first fixed lens group, a first movable lens group, a second movable lens group, and a second fixed lens group. The first fixed lens group, the first movable lens group, the second movable lens group, and the second fixed lens group are sequentially disposed from an object side toward the imaging plane.

The first fixed lens group includes one or more lenses. For example, the first fixed lens group includes a lens having a negative refractive power and a lens having a positive refractive power. The lens having the negative refractive power is adjacently disposed to an object-side surface of a prism, and the lens having the positive refractive power is adjacently disposed to an image-side surface of the prism.

The first movable lens group includes one or more lenses. For example, the first movable lens group includes three lenses. The three lenses are lenses having different refractive powers. For example, the first movable lens group includes two lenses having a negative refractive power and one lens having a positive refractive power. However, a combination of the lenses configuring the first movable lens group is not limited to the described example. In accordance with another example, the first movable lens group includes two lenses having positive refractive power and one lens having negative refractive power.

The second movable lens group includes one or more lenses. For example, the second movable lens group includes one lens having a negative refractive power. However, the second movable lens group is not limited to including only one lens. For example, the second movable lens group may include three lenses. In another configuration, the one lens has a positive refractive power.

The second fixed lens group includes one or more lenses. For example, the second fixed lens group includes one lens having a positive refractive power. In another configuration, the one lens has a negative refractive power.

The optical imaging system includes the prism, a reflecting member, a filter, the stop, and an image sensor.

The prism is disposed in the first fixed lens group. For example, the prism is disposed between or adjacent to the lenses configuring the first fixed lens group. The prism is formed of a material having a substantially low refractive power. For example, the prism has a refractive power of 2.1 or less. In a case in which the prism has the substantially low refractive power, manufacturing costs of the optical imaging system may be reduced.

The reflecting member is disposed between the second fixed lens group and the image sensor. The reflecting member reflects light refracted by the prism to resolve a phenomenon in which the optical imaging system is elongated in one direction.

The filter is disposed between the reflecting member and the image sensor. The filter filters a partial wavelength of incident light to improve resolution of the optical imaging system. For example, the filter filters an infrared wavelength of the incident light.

The stop is disposed in order to adjust an amount of light incident to the lenses. For example, the stop is disposed between the first movable lens group and the second movable lens group.

In accordance with an embodiment, the optical imaging system satisfies the following Conditional Expressions 1 through 4:

$2.0 < ft/fw$      [Conditional Expression 1]

$np < 2.1$      [Conditional Expression 2]

$4.5 < BFL$      [Conditional Expression 3]

$Yh/(IMG\ HT) < 0.55.$      [Conditional Expression 4]

In one example, ft is an overall focal length at a telephoto end, where end is an end of a zoom range, fw is an overall focal length at a wide angle end, np is a refractive index of the prism, BFL is a distance from an image-side surface of a lens closest to the imaging plane in the second fixed lens group to the imaging plane, Yh is ½ of a length of a short side of the imaging plane, and IMG HT is ½ of a diagonal length of the imaging plane.

In one embodiment, the optical imaging system meeting the Conditional Expressions 1 through 4 enable miniaturization of the optical imaging system.

Next, optical imaging systems, according to several embodiments, will be described.

An optical imaging system, according to a first embodiment, will be described with reference to FIG. 1.

The optical imaging system 1000, according to the first embodiment, includes an optical system including a first lens 1010, a second lens 1020, a third lens 1030, a fourth lens 1040, a fifth lens 1050, a sixth lens 1060, a seventh lens 1070, an eighth lens 1080, a ninth lens 1090, a tenth lens 1100, and an eleventh lens 1110.

The lenses configuring the optical imaging system 1000 may be grouped into a plurality of lens groups. For example, the first lens 1010 and the second lens 1020 configure a first fixed lens group Gf1, the third to fifth lens 1030 to 1050 configure a first movable lens group Gm1, the sixth lens 1060 and the seventh lens 1070 configure a correction lens group Go, the eighth to tenth lenses 1080 to 1100 configure a second movable lens group Gm2, and the eleventh lens 1110 configures a second fixed lens group Gf2.

The first movable lens group Gm1 changes an overall focal length of the optical imaging system 1000. For example, a focal length of the optical imaging system 1000 changes within a range of 4.80 to 13.56, depending on a position of the first movable lens group Gm1.

The second movable lens group Gm2 adjusts the overall focal length of the optical imaging system 1000. For example, the focal length of the optical imaging system 1000 may be finely adjusted depending on a position of the second movable lens group Gm2.

The correction lens group Go corrects shaking of the optical imaging system 1000. For example, the correction lens group Go moves in an optical axis direction or a direction intersecting with an optical axis, and corrects noise or vibration generated due to the shaking of the optical imaging system 1000.

Next, the lenses configuring each lens group will be described in detail.

The first lens 1010 has a refractive power. For example, the first lens 1010 has a negative refractive power. The first lens 1010 has a meniscus shape. For example, an object-side surface of the first lens 1010 is convex, and an image-side surface thereof is concave.

The second lens 1020 has a refractive power. For example, the second lens 1020 has a positive refractive power. One surface of the second lens 1020 may be convex. For example, both surfaces of the second lens 1020 are convex.

The third lens 1030 has a refractive power. For example, the third lens 1030 has a negative refractive power. The third lens 1030 has a meniscus shape. For example, an object-side surface of the third lens 1030 is convex, and an image-side surface thereof is concave.

The fourth lens 1040 has a refractive power. For example, the fourth lens 1040 has a negative refractive power. The fourth lens 1040 has a meniscus shape. For example, both surfaces of the fourth lens 1040 are concave.

The fifth lens 1050 has a refractive power. For example, the fifth lens 1050 has a positive refractive power. The fifth lens 1050 has a meniscus shape. For example, an object-side surface of the fifth lens 1050 is convex, and an image-side surface thereof is concave. The fifth lens 1050 configured as described above may be cemented to an image-side surface of the fourth lens 1040. In other words, the object-side surface of the fifth lens 1050 is configured with a convex curvature to be able to be enabled to be fit and contact with the image-side surface of the fourth lens 1040. In accordance with an alternative embodiment, the object-side surface of the fifth lens 1050 is configured with a convex curvature with a curvature corresponding to the image-side surface of the fourth lens 1040 and at a predetermined distance from the image-side surface of the fourth lens 1040.

The sixth lens 1060 has a refractive power. For example, the sixth lens 1060 has a positive refractive power. The sixth lens 1060 has a meniscus shape. For example, an object-side surface of the sixth lens 1060 is convex, and an image-side surface thereof is concave.

The seventh lens 1070 has a refractive power. For example, the seventh lens 1070 has a negative refractive power. The seventh lens 1070 has a meniscus shape. For example, an object-side surface of the seventh lens 1070 is convex, and an image-side surface thereof is concave. In an alternative example, the object-side surface of the seventh lens 1070 is concave, and an image-side surface thereof is concave.

The eighth lens 1080 has a refractive power. For example, the eighth lens 1080 has a positive refractive power. At least one surface of the eighth lens 1080 is convex. For example, both surfaces of the eighth lens 1080 are convex.

The ninth lens 1090 has a refractive power. For example, the ninth lens 1090 has a positive refractive power. At least one surface of the ninth lens 1090 is convex. For example, both surfaces of the ninth lens 1090 are convex.

The tenth lens 1100 has a refractive power. For example, the tenth lens 1100 has a negative refractive power. The tenth lens 1100 has a meniscus shape. For example, both surfaces of the tenth lens 1100 are concave. The tenth lens 1100 configured as described above may be cemented to an image-side surface of the ninth lens 1090. In other words, the object-side surface of the tenth lens 1100 is configured with a concave curvature to be able to be enabled to be fit and contact with the image-side surface of the ninth lens 1090. In accordance with an alternative embodiment, the object-side surface of the tenth lens 1100 is configured with a concave curvature with a curvature corresponding to the image-side surface of the ninth lens 1090 and at a predetermined distance from the image-side surface of the ninth lens 1090.

The eleventh lens 1110 has a refractive power. For example, the eleventh lens 1110 has a positive refractive power. At least one surface of the eleventh lens 1110 is convex. For example, both surfaces of the eleventh lens 1110 is convex.

In the configurations of the lenses as described above, the first lens 1010 are divergently disposed or not in parallel with the second to eleventh lenses 1020 to 1110. For example, an optical axis of the first lens 1010 may intersect with an optical axis of the second to eleventh lenses 1020 to 1110.

The optical imaging system 1000 includes a prism P, a stop ST, a reflecting member M, a filter 1120, and an image sensor 1130.

The prism P is disposed between or adjacent to the first lens 1010 and the second lens 1020. The prism P disposed as described above refracts light irradiated from the first lens 1010 to the second lens 1020.

The stop ST is disposed between the first movable lens group Gm1 and the second movable lens group Gm2 or between the correction lens group Go and the second movable lens group Gm2. In detail, the stop ST is disposed between the seventh lens 1070 and the eighth lens 1080. The stop ST disposed as described above adjusts an amount of light irradiated from the first movable lens group Gm1.

The reflecting member M is disposed between the eleventh lens 1110 and the filter 1120. The reflecting member M reflects light irradiated from the eleventh lens 1110 to the image sensor 1130.

The filter 1120 is disposed between the reflecting member M and the image sensor 1130. The filter 1120 filters infrared rays, or the like, from the light reflected from the reflecting member M.

The image sensor 1130 includes a plurality of optical sensors. The image sensor 1130 converts an optical signal into an electrical signal.

Figure 2:
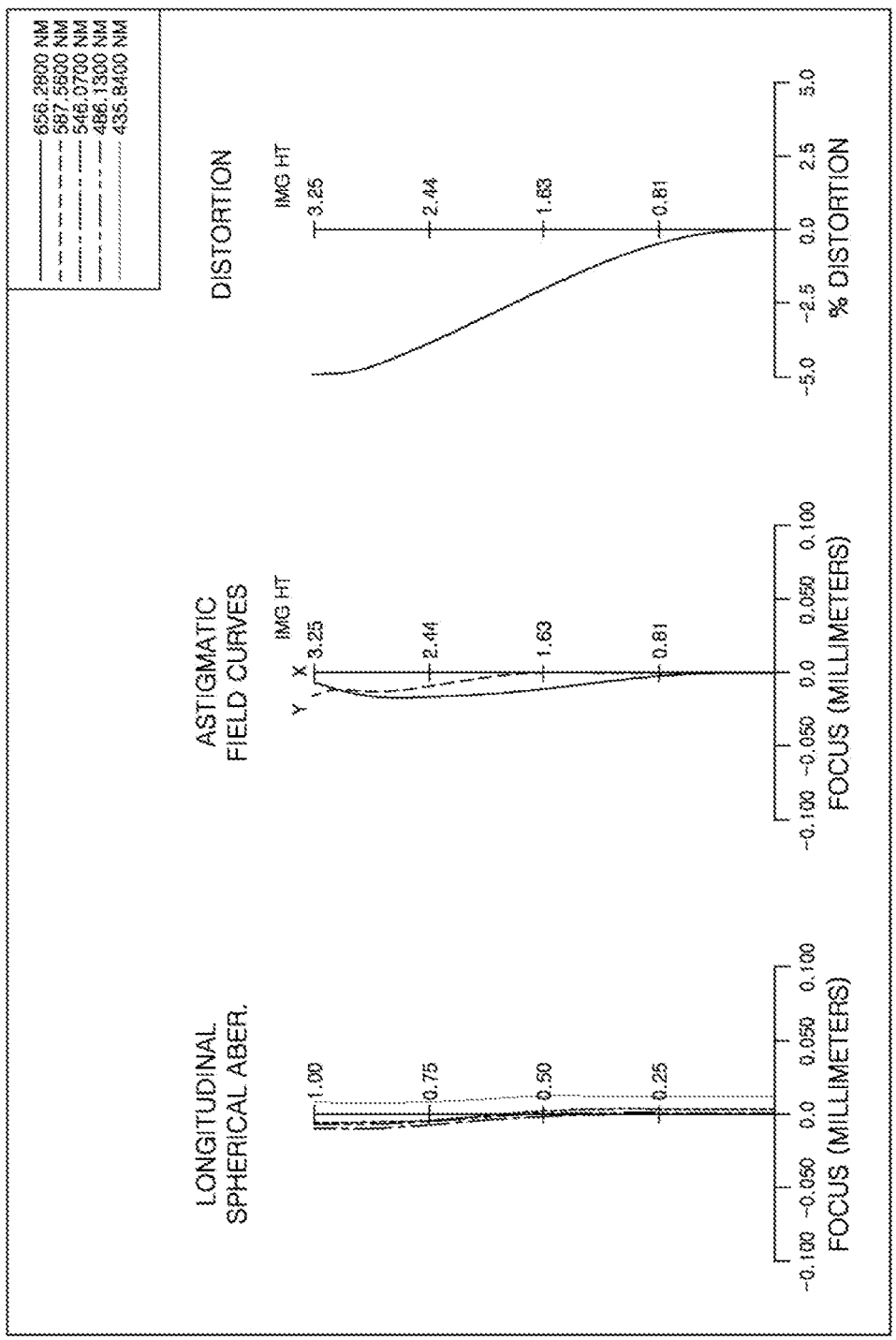
FIG. 2 illustrates graphs aberration curves at a wide angle end of the optical imaging system, according to the first embodiment.
Figure 3:
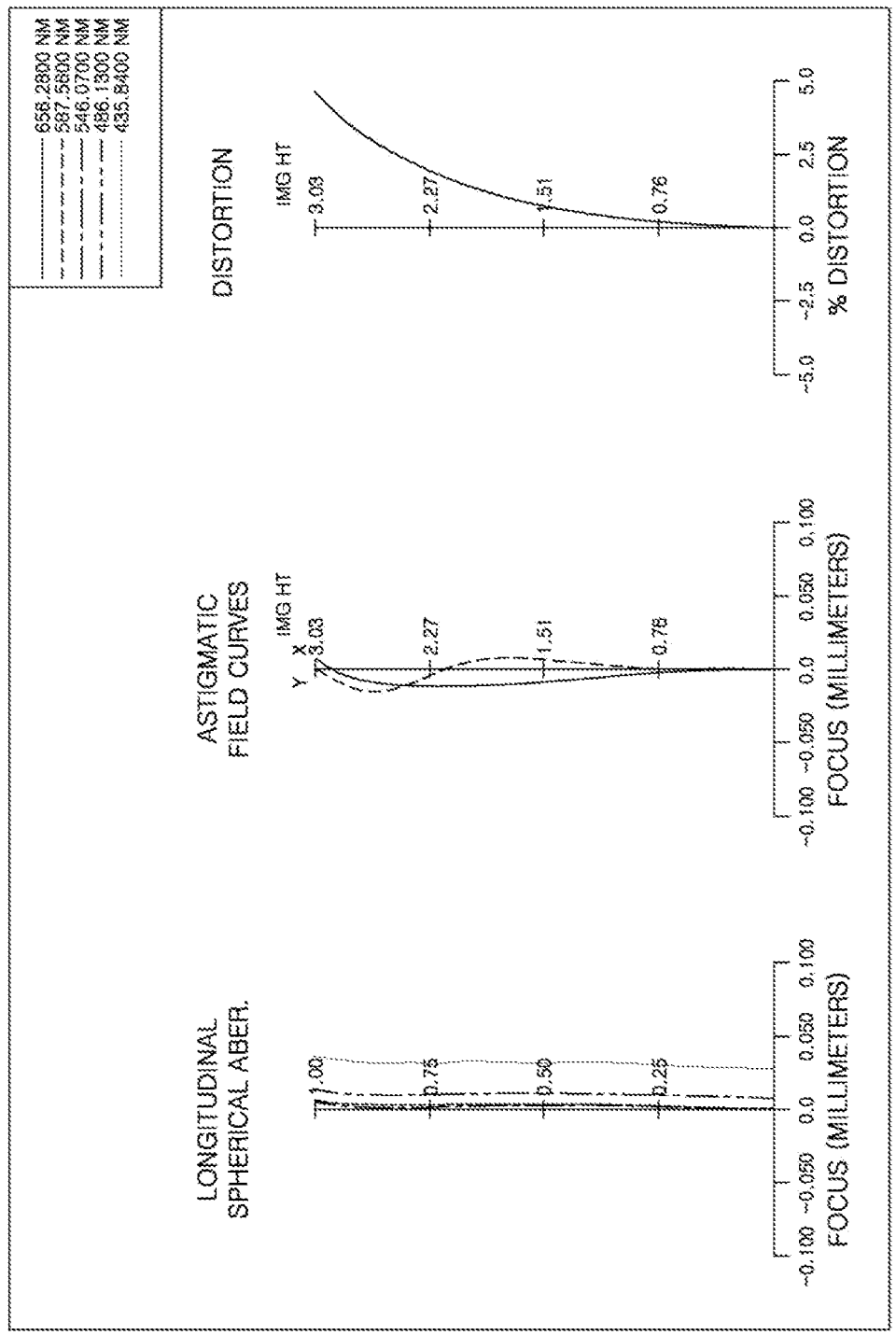
FIG. 3 illustrates graphs aberration curves at an intermediate end of the optical imaging system, according to the first embodiment.
Figure 4:
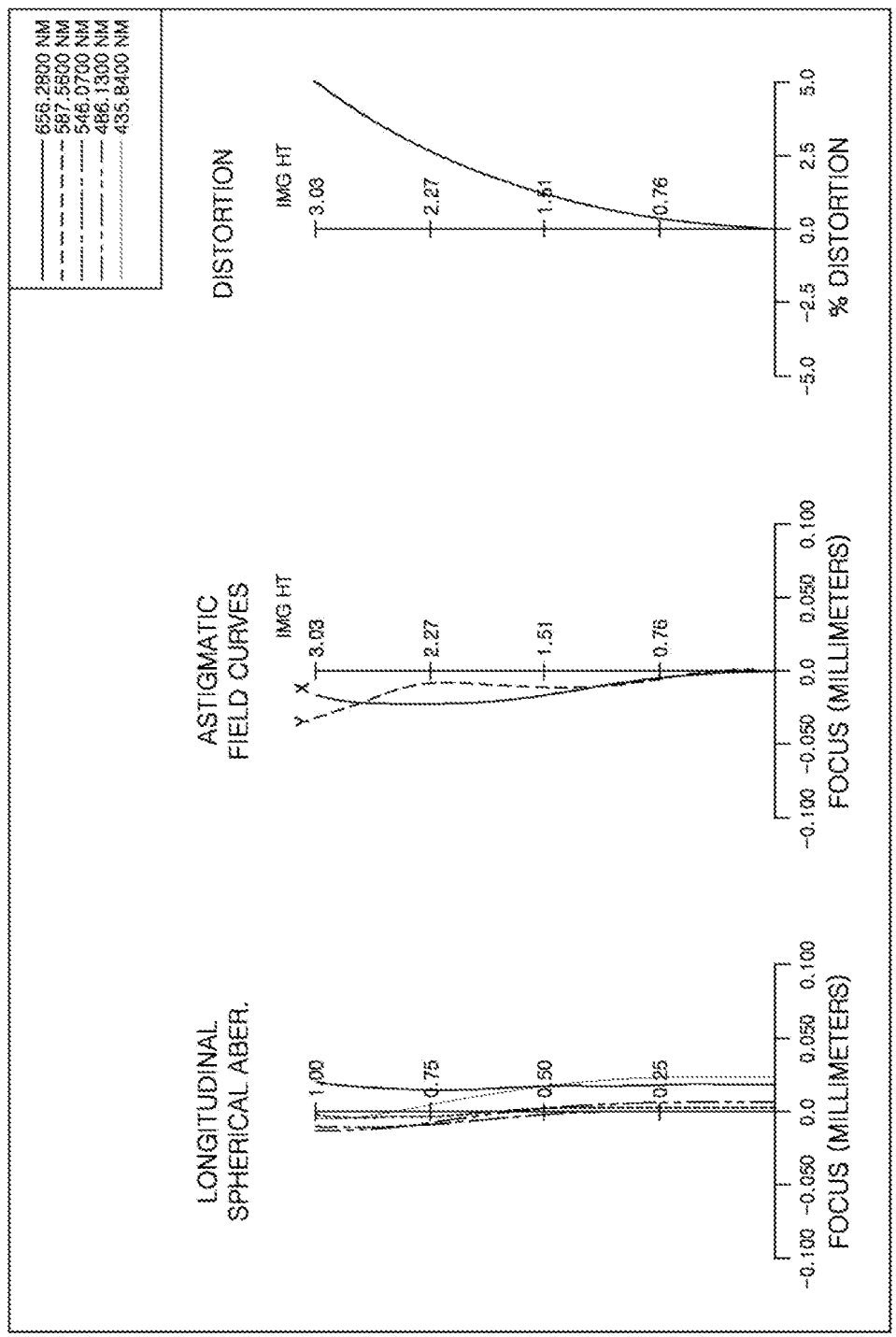
FIG. 4 illustrates graphs aberration curves at a telephoto end of the optical imaging system, according to the first embodiment.

The optical imaging system configured as described above may represent aberration characteristics illustrated in FIGS. 2 through 4. FIG. 2 are graphs illustrating aberration curves in a wide angle end position; FIG. 3 illustrates graphs aberration curves in an intermediate end position; and FIG. 4 illustrates graphs aberration curves in a telephoto end position.

FIG. 5 is a table illustrating characteristics of lenses of the optical imaging system according to the first exemplary embodiment. FIG. 6 is a table illustrating magnitudes of D1, D2, D3, D4, and D5 depending on the wide angle end, the intermediate end, and the telephoto end positions. FIG. 7 is a table illustrating aspherical characteristics of the optical imaging system, according to the first embodiment.

As seen in FIG. 6, a distance D1 between the first fixed lens group Gf1 and the first movable lens group Gm1 is shortest at the wide angle end and is longest at the telephoto end. Similarly, a distance D4 between the second movable lens group Gm2 and the second fixed lens group Gf2 are shortest at the wide angle end and be longest at the telephoto end.

In contrast, a distance D2 between the first movable lens group Gm1 and the correction lens group Go is longest at the wide angle end and is shortest at the telephoto end. Similarly, a distance D3 between the correction lens group Go and the second movable lens group Gm2 is longest at the wide angle end and shortest at the telephoto end.

A distance D5 between the second fixed lens group Gf2 and the image sensor 1130 is constant or substantially constant regardless of the wide angle end, the intermediate end, and the telephoto end.

An optical imaging system, according to a second embodiment, will be described with reference to FIG. 8.

The optical imaging system 2000, according to the second embodiment, includes an optical system including a first lens 2010, a second lens 2020, a third lens 2030, a fourth lens 2040, a fifth lens 2050, a sixth lens 2060, a seventh lens 2070, and an eighth lens 2080.

The lenses configuring the optical imaging system 2000 are grouped into a plurality of lens groups. For example, the first to third lenses 2010 to 2030 configure a first fixed lens group Gf1, the fourth to sixth lenses 2040 to 2060 configure a first movable lens group Gm1, the seventh lens 2070 configures a second movable lens group Gm2, and the eighth lens 2080 configures a second fixed lens group.

The first movable lens group Gm1 changes an overall focal length of the optical imaging system 2000. For example, a focal length of the optical imaging system 2000 is changed in a range of 4.90 to 13.70 depending on a position of the first movable lens group Gm1.

The second movable lens group Gm2 adjusts the overall focal length of the optical imaging system 2000. For example, the focal length of the optical imaging system 2000 is finely adjusted depending on a position of the second movable lens group Gm2.

Next, the lenses configuring each lens group will be described in detail.

The first lens 2010 has a refractive power. For example, the first lens 2010 has a negative refractive power. The first lens 2010 has a meniscus shape. For example, an object-side surface of the first lens 2010 is convex, and an image-side surface thereof is concave.

The second lens 2020 has a refractive power. For example, the second lens 2020 has a negative refractive power. The second lens 2020 has a meniscus shape. For example, both surfaces of the second lens 2020 are concave.

The third lens 2030 has a refractive power. For example, the third lens 2030 has a positive refractive power. The third lens 2030 has a meniscus shape. For example, an object-side surface of the third lens 2030 is convex, and an image-side surface thereof is concave. The third lens 2030 is cemented to an image-side surface of the second lens 2020. In other words, the object-side surface of the third lens 2030 is configured with a convex curvature to be able to be enabled to be fit and contact with the image-side surface of the second lens 2020. In accordance with an alternative embodiment, the object-side surface of the third lens 2030 is configured with a convex curvature with a curvature corresponding to the image-side surface of the second lens 2020 and at a predetermined distance from the image-side surface of the second lens 2020.

The fourth lens 2040 has a refractive power. For example, the fourth lens 2040 has a positive refractive power. At least one surface of the fourth lens 2040 is convex. For example, both surfaces of the fourth lens 2040 are convex.

The fifth lens 2050 has a refractive power. For example, the fifth lens 2050 has a negative refractive power. The fifth lens 2050 has a meniscus shape. For example, an object-side surface of the fifth lens 2050 is convex, and an image-side surface of the fifth lens 2050 is concave.

The sixth lens 2060 has a refractive power. For example, the sixth lens 2060 has a positive refractive power. At least one surface of the sixth lens 2060 is convex. For example, both surfaces of the sixth lens 2060 are convex. The sixth lens 2060 formed as described above is cemented to the image-side surface of the fifth lens 2050. In other words, the object-side surface of the sixth lens 2060 is configured with a convex curvature to be able to be enabled to be fit and contact with the image-side surface of the fifth lens 2050. In accordance with an alternative embodiment, the object-side surface of the sixth lens 2060 is configured with a convex curvature with a curvature corresponding to the image-side surface of the fifth lens 2050 and at a predetermined distance from the image-side surface of the fifth lens 2050.

The seventh lens 2070 has a refractive power. For example, the seventh lens 2070 has a negative refractive power. The seventh lens 2070 has a meniscus shape. For example, both surfaces of the seventh lens 2070 is concave.

The eighth lens 2080 has a refractive power. For example, the eighth lens 2080 has a positive refractive power. At least one surface of the eighth lens 2080 is convex. For example, both surfaces of the eighth lens 2080 is convex.

In the configurations of the lenses as described above, the first lens 2010 are divergently disposed or not in parallel with the second to eighth lenses 2020 to 2080. For example, an optical axis of the first lens 2010 intersect with optical axes of the second to eighth lenses 2020 to 2080.

The optical imaging system 2000 includes a prism P, a stop ST, a reflecting member M, a filter 2120, and an image sensor 2130.

The prism P is disposed between or adjacent to the first lens 2010 and the second lens 2020. The prism P disposed as described above refracts light irradiated from the first lens 2010 to the second lens 2020.

The stop ST is disposed between the first movable lens group Gm1 and the second movable lens group Gm2. In detail, the stop ST is disposed between the sixth lens 2060 and the seventh lens 2070. The stop ST disposed, as described above, adjusts an amount of light irradiated from the first movable lens group Gm1.

The reflecting member M is disposed between the eighth lens 2080 and the filter 2120. The reflecting member M reflects light irradiated from the eleventh lens 2080 to the image sensor 2130.

The filter 2120 is disposed between the reflecting member M and the image sensor 2130. The filter 2120 filters an infrared ray, or other light rays, in the light reflected from the reflecting member M.

The image sensor 2130 includes a plurality of optical sensors. The image sensor 2130 coverts an optical signal into an electrical signal.

Figure 9:
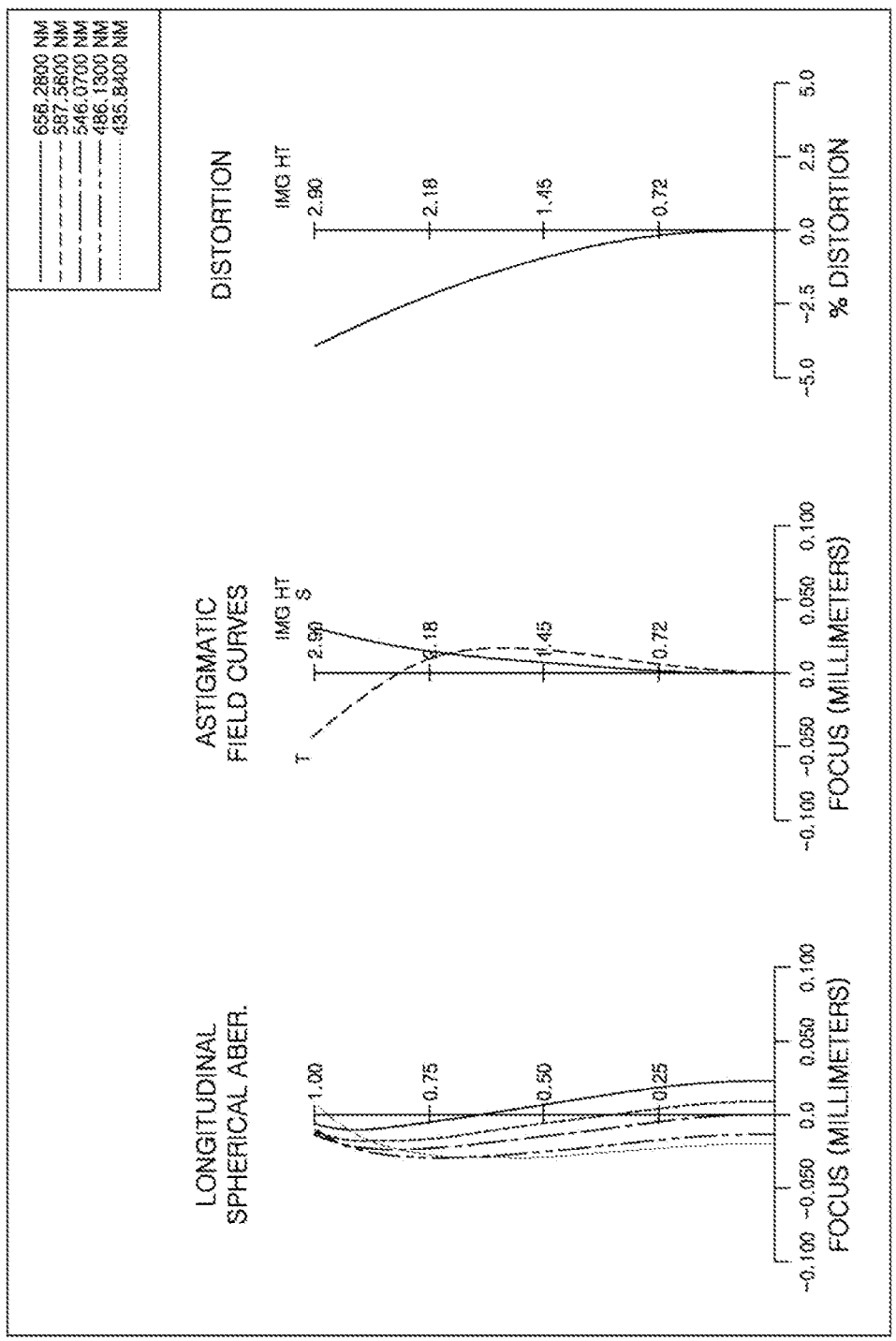
FIG. 9 illustrates graphs aberration curves at a wide angle end of the optical imaging system, according to the second embodiment.
Figure 10:
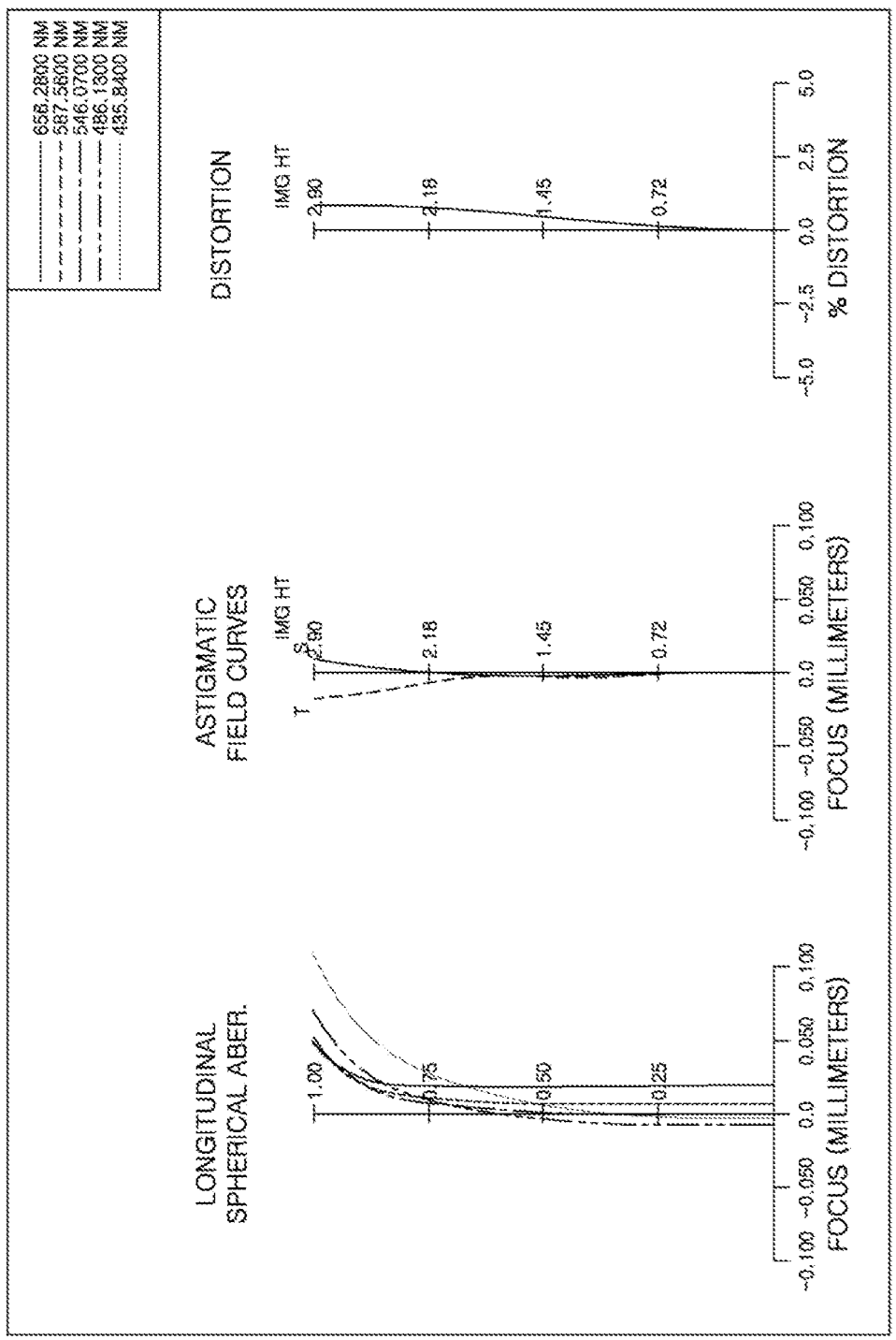
FIG. 10 illustrates graphs aberration curves at an intermediate end of the optical imaging system, according to the second embodiment.
Figure 11:
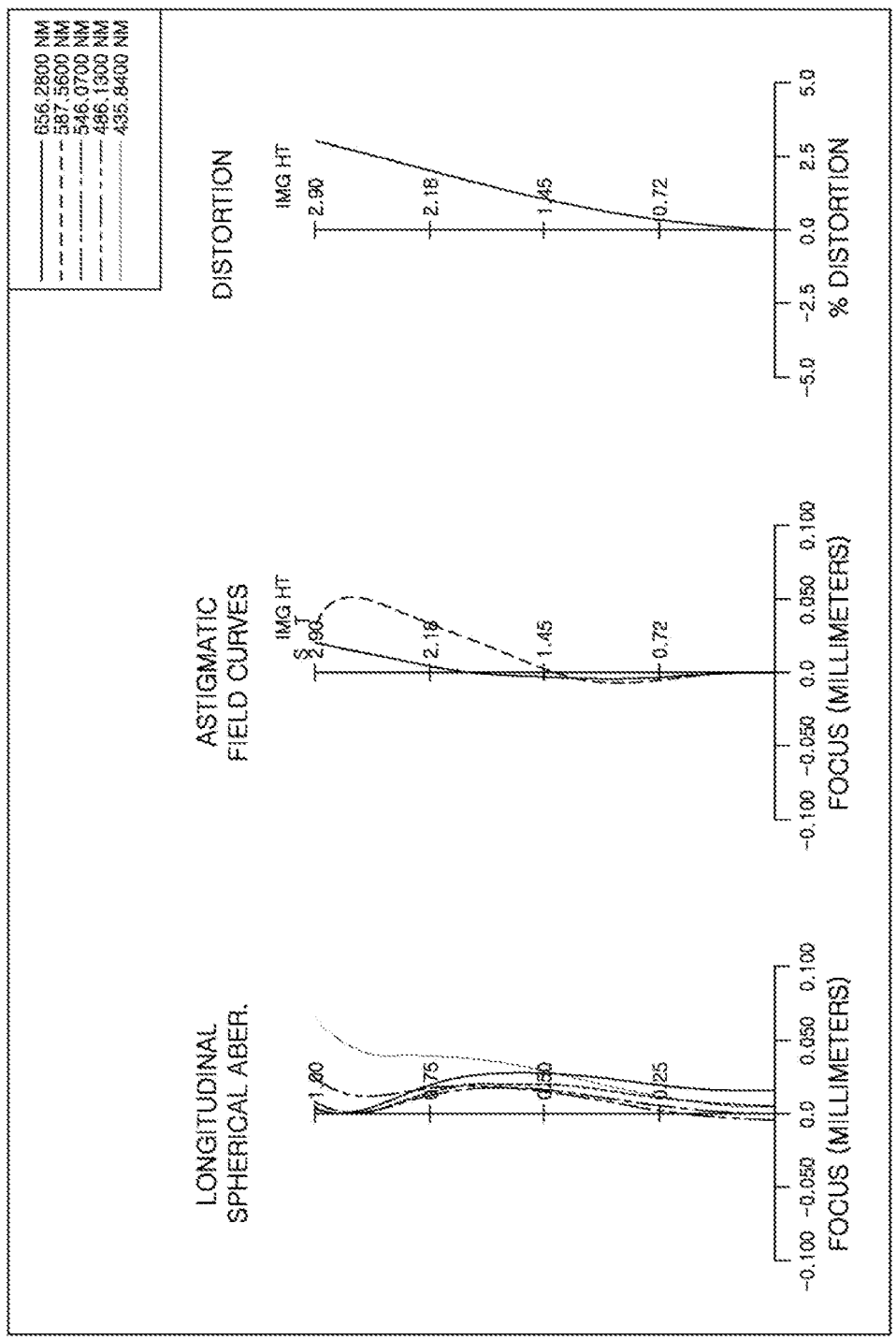
FIG. 11 illustrates graphs aberration curves at a telephoto end of the optical imaging system, according to the second embodiment.

The optical imaging system, configured as described above, may represent aberration characteristics illustrated in FIGS. 9 through 11. FIG. 9 illustrates graphs aberration curves in a wide angle end position; FIG. 10 illustrates graphs aberration curves in an intermediate end position; and FIG. 11 illustrates graphs aberration curves in a telephoto end position.

FIG. 12 is a table illustrating characteristics of lenses of the optical imaging system, according to the second embodiment. FIG. 13 is a table illustrating magnitudes of D1, D2, and D3 depending on a wide angle end, an intermediate end, and telephoto end positions. FIG. 14 is a table illustrating aspherical characteristics of the optical imaging system, according to the second embodiment.

As seen in FIG. 13, a distance D1 between the first fixed lens group Gf1 and the first movable lens group Gm1 may be longest at the wide angle end and be shortest at the telephoto end.

In contrast, a distance D2 between the first movable lens group Gm1 and the second movable lens group Gm2 may be shortest at the wide angle end and be longest at the telephoto end. Further, a distance D3 between the second movable lens group Gm2 and the second fixed lens group Gf2 may be shortest at the wide angle end and be longest at the telephoto end.

Table 1 represents calculated values of the optical imaging systems, according to the first and second embodiments, with respect to Conditional Expressions 1 through 4.

TABLE 1

| Conditional Expression | First Embodiment | Second Embodiment |
| --- | --- | --- |
| ft/fw | 2.825 | 2.80 |
| np | 2.001 | 1.91082 |
| BFL | 5.897 | 4.910 |

As set forth above, according to various embodiments, an optical imaging system of which optical performance may be improved is realized.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An optical imaging system, comprising:
    a first fixed lens group comprising lenses having different refractive powers;
    a prism disposed between the lenses of the first fixed lens group;
    a first movable lens group configured to be movable to change an overall focal length;
    a correction lens group configured to move in an optical axis direction or a direction intersecting with the optical axis;
    a second movable lens group configured to be movable to finely adjust the overall focal length; and
    a second fixed lens group,
    wherein a distance between the first movable lens group and the correction lens group is longest at a wide angle end and is shortest at a telephoto end,
    wherein a distance between the correction lens group and the second movable lens group is longest at the wide angle end and shortest at the telephoto end,
    wherein the correction lens group is disposed between the first movable lens group and the second movable lens group, and wherein the second movable lens group includes two lenses each having positive refractive power.

2. The optical imaging system of claim 1, wherein a distance between the first fixed lens group and the first movable lens group is shortest at the wide angle end and is longest at the telephoto end.

3. The optical imaging system of claim 1, wherein a distance between the second movable lens group and the second fixed lens group are shortest at the wide angle end and longest at the telephoto end.

4. The optical imaging system of claim 1, wherein a distance between the second fixed lens group and the image sensor is constant or substantially constant.

5. The optical imaging system of claim 1, wherein 4.5<BFL, in which BFL is a distance from an image-side surface of a lens closest to an imaging plane in the second fixed lens group to the imaging plane.

6. The optical imaging system of claim 1, wherein the correction lens group consists essentially of two lenses.

7. The optical imaging system of claim 1, wherein the first fixed lens group, the first movable lens group, the correction lens group, the second movable lens group, and the second fixed lens group are disposed in this order from an object side toward an image side of the optical imaging system.

8. An optical imaging system, comprising:
a first fixed lens group comprising lenses having different refractive powers;
a prism disposed between the lenses of the first fixed lens group;
a first movable lens group configured to be movable to change an overall focal length;
a correction lens group configured to move in an optical axis direction or a direction intersecting with the optical axis;
a second movable lens group configured to be movable to finely adjust the overall focal length; and
a second fixed lens group,
wherein a distance between the first movable lens group and the correction lens group is longest at a wide angle end and is shortest at a telephoto end,
wherein a distance between the correction lens group and the second movable lens group is longest at the wide angle end and shortest at the telephoto end,
wherein the correction lens group consists essentially of two lenses, and
wherein the second movable lens group includes two lenses each having positive refractive power.

9. The optical imaging system of claim 8, wherein a distance between the first fixed lens group and the first movable lens group is shortest at the wide angle end and is longest at the telephoto end.

10. The optical imaging system of claim 8, wherein a distance between the second movable lens group and the second fixed lens group are shortest at the wide angle end and longest at the telephoto end.

11. The optical imaging system of claim 8, wherein a distance between the second fixed lens group and the image sensor is constant or substantially constant.

12. The optical imaging system of claim 8, wherein 4.5<BFL, in which BFL is a distance from an image-side surface of a lens closest to an imaging plane in the second fixed lens group to the imaging plane.

13. The optical imaging system of claim 8, wherein the first fixed lens group, the first movable lens group, the correction lens group, the second movable lens group, and the second fixed lens group are disposed in this order from an object side toward an image side of the optical imaging system.

14. An optical imaging system, comprising:
a first fixed lens group comprising lenses having different refractive powers;
a prism disposed between the lenses of the first fixed lens group;
a first movable lens group configured to be movable to change an overall focal length;
a correction lens group configured to move in an optical axis direction or a direction intersecting with the optical axis;
a second movable lens group configure d to be movable to finely adjust the overall focal length; and
a second fixed lens group,
wherein the first fixed lens group, the first movable lens group, the correction lens group, the second movable lens group, and the second fixed lens group are disposed in this order from an object side toward an image side of the optical imaging system,
wherein a distance between the first movable lens group and the correction lens group is longest at a wide angle end and is shortest at a telephoto end,
wherein a distance between the correction lens group and the second movable lens group is longest at the wide angle end and shortest at the telephoto end, and
wherein the second movable lens group includes two lenses each having positive refractive power.

15. The optical imaging system of claim 14, wherein a distance between the first fixed lens group and the first movable lens group is shortest at the wide angle end and is longest at the telephoto end.

16. The optical imaging system of claim 14, wherein a distance between the second movable lens group and the second fixed lens group are shortest at the wide angle end and longest at the telephoto end.

17. The optical imaging system of claim 14, wherein a distance between the second fixed lens group and the image sensor is constant or substantially constant.

18. The optical imaging system of claim 14, wherein 4.5<BFL, in which BFL is a distance from an image-side surface of a lens closest to an imaging plane in the second fixed lens group to the imaging plane.

* * * * *

UNITED STATES PATENT AND TRADEMARK OFFICE
CERTIFICATE OF CORRECTION

PATENT NO. : 11,079,572 B2
APPLICATION NO. : 16/460232
DATED : August 3, 2021
INVENTOR(S) : Hag Chul Kim Page 1 of 1

It is certified that error appears in the above-identified patent and that said Letters Patent is hereby corrected as shown below:

On the Title Page

"Related U.S. Application Data" in item (62), delete "Division of application No. 15/098,989," and insert --Division of application No. 15/092,989,--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*